United States Patent [19]

Tomiyama et al.

[11] 4,321,058
[45] Mar. 23, 1982

[54] LATEX COMPOSITION AND METHOD FOR DETERMINING ERYTHROPOIETIN

[75] Inventors: Tetsuo Tomiyama, Ohizumigakuen; Takashi Ogura, Higashiyamato, both of Japan

[73] Assignee: Seikagaku Kogyoco Ltd., Tokyo, Japan

[21] Appl. No.: 162,897

[22] Filed: Jun. 25, 1980

[30] Foreign Application Priority Data

Jun. 28, 1979 [JP] Japan .................. 54/80741

[51] Int. Cl.$^3$ ........................................... G01N 33/54
[52] U.S. Cl. .................................... 23/230 B; 424/12
[58] Field of Search ..................... 23/230 B; 424/12

[56] References Cited

U.S. PATENT DOCUMENTS 4,062,936 12/1977 Ogawa ........................... 424/12
4,136,161 1/1979 Falkowski ................... 424/12 X
4,254,095 3/1981 Fisher ........................... 23/230 B X

OTHER PUBLICATIONS

Chemical Abstracts, 83: 144027a, (1975).

*Primary Examiner*—Sidney Marantz
*Attorney, Agent, or Firm*—Sherman & Shalloway

[57] ABSTRACT

A composition for determining human erythropoietin, said composition consisting essentially of synthetic polymeric latex particles and human erythropoietin coated on the surface of said latex particles; and a method for determining human erythropoietin in human urine or serum by the microtiter method using aforesaid composition.

8 Claims, No Drawings

LATEX COMPOSITION AND METHOD FOR DETERMINING ERYTHROPOIETIN

This invention relates to a composition for determining human erythropoietin, a process for its preparation and a method for determining human erythropoietin.

Specifically, the invention relates to a composition for determining human erythropoietin, the use of which, as contrasted with the extremely complicated, time-consuming and costly bioassay means that has been practiced hitherto, makes it possible to determine (both quantitatively and qualitatively) with accuracy and precision the human erythropoietin contained in a humor sample by an easy assay means using a simple instrument. In addition, it makes it possible to make an accurate etiologic analysis of anemic patients as well as evaluate the results of therapeutic treatments administered and make a prognosis of the disease. The invention also relates to a process for preparing the foregoing composition as well as to a method of determining human erythropoietin.

More specifically, this invention relates to a composition for determining human erythropoietin, which consists essentially of synthetic polymeric latex particles, preferably particles of a styrene-type synthetic polymeric latex selected from the group consisting of styrene polymer, styrene copolymers and the carboxylated products or amino-containing carboxylated products thereof; to a process for the preparation of the composition; and to the use of the composition.

The life of human erythrocytes is about 120 days, and 1/120 of the total erythrocytes is destroyed daily in the reticulo-endothelial system. Concurrently, the same number of erythrocytes are produced to maintain the number of erythrocytes constant at all times.

The erythrocytes are produced by the maturation and differentiation of the erythroblasts in the bone marrow, and erythropoietin is a factor which by acting on the undifferentiated stem cells induces their differentiation to erythrocytes. The secretion of erythropoietin is accelerated when there is a drop in the oxygen partial pressure of the body tissues. Thus, erythropoietin is a humoral hormone which controls the number of erythrocytes that are produced in the bone marrow.

In the case of mammals all or a major portion of this erythropoietin is produced in the kidney by glycoprotein containing sialic acid whose molecular weight is estimated to be about 27,000–66,000.

The disorders in which human erythrocytes decreases, i.e. anemia, can be roughly classified etiologically into three types. The first type is that where the stem cells, the origin of the erythrocytes, are anomalous and thus the erythrocytes cannot be produced even though the productive ability of the erythropoietin is normal, i.e. aplastic anemia. This anomaly of the stem cells may be further divided into such cases as the hypoplasty of the bone marrows, anomaly of the bone marrow itself, inadequacy of the sites where the erythrocytes proliferate, and a decline in the reactivity to erythropoietin. In the case of anemic disorders of this kind the mechanism of the body which tends to increase the number of erythrocytes comes into action, with the consequence that the amount of erythropoietin exhibits an extremely or abnormally high value. The second type of anemia is that such as chronic renal insufficiency, i.e. anemia of renal diseases. In this case, since this is an organic disorder of the kidneys, the producer of erythropoietin, erythropoietin cannot be produced even though the stem cells are normal. Hence, an increase in the number of erythrocytes cannot be had, thus resulting in anemia. In this case only a low concentration of erythropoietin is present in the humor. The third type of anemia is the case where both the stem cells and the erythropoietin productive ability are normal, the anemic condition being that ascribable to iron deficiency, hemorrhage, vitamin $B_{12}$ deficiency, hemolysis ascribable to autoimmunity, etc. In this case the amount of erythropoietin shows a high value and a negative correlation with the amount of hemoglobin.

While anemia itself can be readily diagnosed by a count of the actual number of erythrocytes, measurement of the hematocyte volume by the hematocrit method or measurement of hemoglobin, the diagnosis of the cause of the anemic condition: whether the cause of the disorder is ascribable to an anomaly of the stem cells, whether it is due to insufficient production of erythropoietin ascribable to renal disorders, or whether the cause can be ascribed to causes other than the foregoing causes, is extremely important in setting up the course of treatment, and making a prognosis of the disease. Again, a determination of the erythropoietin in the humor is indispensable for this purpose.

Hitherto, the method of determination employed was however the bioassay means, a complicated as well as a time-consuming and costly procedure. In this method the amount of erythropoietin is calculated in the following manner. Polythythemic mice or starved rats are injected with erythropoietin, and then an injection of $^{59}Fe$ is made. The amount of erythropoietin is calculated from rate at which the $^{59}Fe$ is taken into the erythrocytes. While this method excels in its specificity, there are such disadvantages as that large number of animals must be bred for a long period of time and that isotope is used. In addition, the method requires much labor and expenses. It was thus difficult to use it in clinical examinations.

For reducing these disadvantages and troubles, there has been developed a method which comprises coating the erythrocytes in advance with human erythropoietin followed by neutralizing the antierythropoietin antibody with the erythropoietin contained in the sample and thereafter using this sensitized hematocytes in carrying out the inhibition of the antigen-antibody agglutination reaction and making a determination from the results obtained. However, since there is a necessity in this method of removing the nonspecific hemagglutin that is contained in human serum, a treatment for absorbing the hemagglutin must be performed. Further, a test for confirming the removal must inevitably be carried out.

Our researches were carried out with the view of solving these difficulties of the conventional methods and developing a method which could readily measure human erythropoietin specifically with good precision and in a relatively short period of time. It was found by these researches that synthetic polymeric latex particles or particles of a styrene-type synthetic polymeric latex coated with purified human erythropoietin (antigen) can be readily formed and that by using this latex as the assay sample the erythropoietin contained in the humor can be readily and expeditiously determined with good precision by the passive latex agglutination inhibition reaction without the necessity for such a pretreatment as absorbing the humors such as serum and urine by means of a carrier.

To wit, since the erythropoietin (antigen)-coated latex undergoes agglutination by reacting with the antierythropoietin antibody, agglutination of the antigen-coated latex does not take place if this antibody is neutralized in advance with the antigen contained in the sample. If the sample does not contain an antigen, the antibody cannot be neutralized. Hence, agglutination of the antigen-coated latex takes place as a result of this antibody. It thus becomes possible to determine the presence or absence of an antigen by way of the passive latex agglutination inhibition reaction.

Thus, by a procedure consisting of adding prescribed amounts of the antibody to progressively diluted samples to neutralize the erythropoietin contained in the sample and thereafter adding the antigen-coated latex and observing the agglutination reaction pattern that is formed by said latex and the antibody remaining unneutralized, it becomes possible to readily determine the amount of erythropoietin.

There have been no proposals whatsoever to date concerning a composition such as described for determining human erythropoietin, a composition consisting essentially of synthetic polymeric latex particles and human erythropoietin coated on the surface of said latex particles.

It has been further found that this composition reacts with an antierythropoietin antibody that has been added to the assay sample and does not react in the least with other antibodies that may be present in the sample or plasma protein. From the fact that the uncoated latex particles does not react at all with an antierythropoietin antibody, other antibodies or plasma protein, it is presumed that erythropoietin is bonded to the latex particles of the present invention as an antigen. It has thus been found that the determination of human erythropoietin can be performed in accordance with the instant invention easily and with superior precision without the need for subjecting the assay sample to any pretreatments or tests for confirmation of such treatments but by the employment of simple operations and instruments comprising placing a humor and a dilution thereof in say a well of a microplate, adding thereto an antierythropoietin antibody prepared for use in immunization, and thereafter adding the composition of this invention dropwise.

It is an object of this invention therefore to provide a novel and excellent composition for determining human erythropoietin, a process for the preparation thereof, and the use of the aforesaid composition.

The above and other objects and advantages of this invention will become more apparent from the following description.

Various synthetic latex particles can be used for the production of the composition for determining human erythropoietin of this invention. Examples of polymers or copolymers that form such latex include, polystyrene, carboxylated polystyrene, amino-containing carboxylated polystyrene, polyvinyltoluene, styrene-butadiene copolymer, carboxylated styrene-butadiene copolymer, styrene-divinylbenzene copolymer, vinyltoluenetertiary butyl styrene copolymer, polyesters, polyacrylic acid, polymethacrylic acid, polyacrylonitrile, acrylonitrile-butadiene-styrene copolymer, polyvinyl acetate acrylate, polyvinylpyrrolidone and vinyl chloride-acrylate copolymer.

Preferred particles of synthetic polymeric latices are particles of styrene-type synthetic polymeric latices selected from the group consisting of styrene polymer, styrene copolymers such as a copolymer of styrene with a monomer selected from the group consisting of chlorostyrene, methyl methacrylate and vinylidene chloride, and carboxylated or amino-containing carboxylated products thereof. These synthetic polymeric latex particles can be used after pre-treating their surfaces with a nonionic surface active agent. For example, it is preferred to use these particles after causing an ethylene oxide-type nonionic surfactant to be adsorbed thereto in accordance with the method described in Japanese Laid-Open Pat. Publication No. 9716/76 laid open on Jan. 26, 1976. Examples of suitable nonionic surfactants of the ethylene oxide type are a block copolymer of ethylene oxide and polyoxypropylene glycol, polyoxyethylene alkyl ethers and polyoxyethylene alkylaryl ethers.

In the present invention, the synthetic polymer latex particles preferably have an average particle diameter of 0.01 to 10 microns, more preferably 0.1 to 1 micron. To increase the reproducibility of the results of measurement, it is preferred to use particles having a relatively narrow range, say a range of $0.2 \pm 0.005$, of size distribution. The specific gravity of the latex particles is preferably about 0.9 to 1.4, and more preferably about 1.1 to 1.3. In the case where the determination is performed utilizing an agglutination reaction on a slide glass plate, latex particles having a broad range of specific gravity can be used. In the case of the microtiter method, it is preferable to use latex particles having a specific gravity of at least 1.1.

Human erythropoietin that is used in this invention for obtaining the composition composed of synthetic polymeric latex particles and human erythropoietin coated on the surface of the latex particles are found in such humors as blood and urine. While it is possible to use both blood and urine as the starting material in this invention, urine is especially suitable, since it is an excretion and thus readily available. As mentioned in the *Journal of Biological Chemistry*, Vol. 252, 5558–5564 (1977), all of such known means as ethanol precipitation, acetone precipitation, tannic acid precipitation, lithium oxide precipitation, salting out with ammonium sulfate, gel filtration, DEAE-cellulose chromatography, polyacylamide gel chromatography, and kaolin adsorption and dissociation can be used for preparing erythropoietin from the foregoing starting materials.

Since erythropoietin can stand heating at say 100° C. for 15 minutes, it is also effective to submit it to a heat treatment at say about 80°–100° C. for about 10 to about 15 minutes prior to its purification thereby heat-modifying a major portion of the other proteins that may be copresent. The erythropoietin used in this invention may be one that has been obtained by any of the means mentioned above or combinations thereof. However, it is preferred that it is a single protein of high purity, since there is the possibility of side reactions taking place when the purity is low.

An antibody can be obtained by using the purified erythropoietin thus obtained as the antigen and immunizing in customary manner animals having the ability to produce antibody, such as goat, rabbit and guinea pig, by inoculating these animals with the erythropoietin, followed by taking the blood therefrom. Any animal can be used in this case as long it is one from which the antibody can be readily obtained. There is thus imposed no restriction as to the class of animal to be used.

The human erythropoietin determining composition of this invention can be produced by a simple procedure. For example, it can be obtained by contacting the latex particles and the antigen (erythropoietin) in water, a physiological saline or the various buffer solutions of pH 5.5–10, preferably pH 6.4–7.6, at about 4° to about 40° C. for about 30 minutes to about 24 hours with gently stirring with preferably a concentration of the latex particles of 0.05–3% and a concentration of the antigen of 50–1000 miu/ml.

The buffer used may, for example, be a phosphate-buffered saline such as, M/60 Phosphate buffer (pH 7.2) containing 0.15 M NaCl (to be abbreviated to PBS) and a glycine-buffered saline. If desired, about 0.01 to about 0.1% of a protein such as bovine serum albumin (to be abbreviated to BSA) may preferably be added to the antigen solution in order to prevent non-specific agglutination. After the coating reaction, the reaction mixture is washed with an aqueous solvent. The antigen not adsorbed to the latex particles can be completely removed by washing the particles say with these buffers. Again, it is recommended that the latex be suspended in a diluent to keep the antigen uncoated portion of the latex particles saturated with protein.

As diluent, that obtained by adding about 0.1% of BSA to say a glycine-buffered sodium chloride solution or a phosphate-buffered sodium chloride solution to which has been further added 0.01–0.5% of sodium azide ($NaN_3$) is used.

The antigen-coated latex obtained in this manner may be kept stored in a refrigerator suspended in a diluent to a concentration of say about 0.25% by weight, or it may be lyophilized. In carrying out the lyophilization, various amino acids, particularly such amino acids as glycine and sodium glutamate, and/or dextran in such amounts as 0.2–2% by weight in the case of the amino acids and 0.3–3% by weight in the case of dextran may be added to the diluent as stabilizers, after which the antigen-coated latex may be quick-frozen in liquid nitrogen or liquid air and then lyophilized. The preservation period is further prolonged by lyophilization, and the antigen-coated latex lyophilized can usually be stored stably for about two years or more.

Since the antigen-coated latex of this invention is agglutinated by the antierythropoietin antibody, first, an antibody is added to a human humor or its dilution and the antibody is neutralized with the antigen present in the human humor or its dilution. Then, the antigen-coated latex is added to the mixture to allow it to react with the remaining antibody and the agglutination patterns are read.

According to this invention, there is provided a method for determining human erythropoietin by utilizing the foregoing reaction. The method consists in qualitatively or quantitatively determining human erythropoietin in human urine or serum using a composition comprising synthetic polymer latex particles and human erythropoietin coated on the surface of the latex particles.

In performing the determination, means known per se can be utilized, and for example, the level of human erythropoietin in the serum or urine can be easily determined by the microtiter method. According to this means, a given amount of a diluent of the type exemplified hereinabove is poured portionwise onto a microplate, and then a given amount of an assay sample such as the serum or urine is introduced into the first well of the plate and successively diluted with a diluter. On the other hand, a dilution series is prepared in the same way using a standard erythropoietin with known concentrations. A given amount of an antibody is then added to all of the samples and the dilution series, after which the samples are held at room temperature for 15–20 minutes to neutralize the antibody. This is followed by the addition and mixing of a given amount of the antigen-coated latex. After standing for a given period of time at room temperature, the end point of agglutination is observed. The absolute amount of erythropoietin can be determined by comparison with the standard erythropoietin series.

The human erythropoietin measuring composition of this invention in the form of a latex or dried product has the following extremely superior advantages. Specifically, an antibody to the carrier cannot possibly be present. In fact it has not been found. Hence, no pretreatment whatever needs to be administered to the humor to be tested, nor is it necessary to carry out a test to confirm such a pretreatment. The operations for the determination consist of only placing the humor or its dilution in a well of a microplate, adding dropwise thereto of an antibody, and thereafter adding the antigen-coated latex dropwise. Thus, the determination of the erythropoietin can be performed very easily with a simple procedure, and no special technique is required. Moreover, since the antigen is one that has been purified, it is extremely specific. In addition, the sensitivity of the test is fully satisfactory for measurement of human humor. Again, it is possible to carry out the qualitative and quantitative determinations of a number of samples simultaneously.

The determination of the concentration of erythropoietin in the humor which had to be performed hitherto by the extremely complicated bioassay method can now be carried out easily in a short period of time by means of a simple procedure when the antigen-coated latex of this invention is used. It thus becomes possible to conduct an accurate etiologic analysis of anemic patients, as well as to make evaluations of the results of treatments administered and a prognosis of the disease. Further, the invention method can also be used in measuring the concentration of erythropoietin in the step of its production from say urine.

From the fact that this antigen-coated latex only reacts with the antierythropoietin antibody and does not react at all with antibodies other than this or plasma protein, and that a latex uncoated does not react at all with the antierythropoietin antibody, antibodies other than this and plasma protein, it can be said that erythropoietin is bonded to this coated latex.

The invention will now be more fully described by reference to preparation and working examples. It is to be understood that this invention is to be in no way restricted to these examples except as defined in the appended claims.

PREPARATION EXAMPLE 1

Preparation of erythropoietin

Phenol (0.1%) was added to the urine of an anemic patient and, after adding a 4-fold volume of ethanol thereto, the mixture was left standing overnight in a refrigerator. The mixture was then centrifuged at 3000 rpm for 30 minutes, after which the sediment was collected and dissolved in a physiological saline followed by dialysis against a physiological saline overnight. This was then added portionwise to small test tubes, which tubes were dipped in boiling water for 15 minutes followed by centrifuging at high speed. The kaolin adsorption and dissociation operation was carried out on the resulting supernatant liquid. Specifically, kaolin washed 5 times in a physiological saline (Acid Washed Kaolin produced by Fisher Scientific Company) was added in an amount of 10% and, after adjusting the pH to 4.8, the mixture was gently stirred at 4° C. for 24 hours. The kaolin was centrifugally separated at 3000 rpm, collected and washed with an acetate buffer of pH 4.8. It was then suspended in 1 M, NH$_4$OH, stirred gently for one hour at room temperature and centrifuged at 3000 rpm for 30 minutes followed by separating the resulting supernatant liquid. After repeating this operation three times, the supernatant liquids were combined. This sample was dialyzed against a solution containing 0.029 M, NaH$_2$PO$_4$ and 0.029 M, NaCl. Next, the sample was added to DEAE-cellulose that had been equilibrated with a solution containing 0.029 M, NaH$_2$PO$_4$ and 0.029 M, NaCl and gently stirred at room temperature for one hour to cause its adsorption. The DEAE-cellulose was then collected by centrifugation at 2000 rpm, washed in the foregoing solution twice, and thereafter eluted three times in a solution containing 0.05 M, Na$_2$HPO$_4$ and 0.15 M, NaCl. The eluate was then concentrated with Lyphogel (registered trademark: trade name of a polyacrylamide gel produced by Gelman Instrument Co., U.S.A.) followed by gel filtration with Sephadex G-100 (registered trademark: trade name of a linkaged dextran produced by Pharmacia Fine Chemicals, AB. Sweden) and thereafter collecting the active portion. This was again precipitated with ethanol, after which the precipitate was washed in ethanol and, after dissolving in a physiological saline, dialyzed against a physiological saline to give an erythropoietin sample.

PREPARATION EXAMPLE 2

Preparation of an erythropoietin antibody

A sample prepared in the same manner as described hereinabove excepting that the heat treatment was not performed was used as the antigen for immununization. After mixing this antigen with a Freund's incomplete adjuvant, the mixture was subcutaneously injected thrice into rabbits weighing 2-3 kg at 7-day intervals followed by one intramuscular injection. Three weeks later, the sample in solution in a physiological saline was intravenously injected. One week after the final injection, the whole blood was taken from the carotid artery, and the serum was separated in customary manner and thereafter heated at 56° C. for 30 minutes. This was preserved at 4° C. after adding 0.1% of sodium azide. The resulting antiserum was confirmed to be a single antibody from the fact that it forms a single band with an antigen by the Ouchtalony method as well as by immunoelectrophoresis.

EXAMPLE 1

Preparation of an erythropoietin (antigen)-coated latex

A polystyrene latex [SDL 59 (specific gravity 1.18, particle diameter 0.9 micron) produced by Takeda Chemical Industry Company] was dispersed in a mixture of 1 volume of 1/15 M phosphate buffer (pH 7.2) and 3 volumes of a physiological saline (abbreviated hereinafter to PBS) such that the particle concentration would become 0.25%. To the resulting suspension was added in an equal amount of erythropoietin diluted with PBS such that it would be 250 miu (milli immuno chemical unit)/ml. The resulting mixture was held at room temperature for 3 hours and then centrifuged to collect the latex particles, which were washed with PBS and then with a diluent, after which the particles were suspended in a diluent to a concentration of 0.25% to obtain an antigen-coated latex. Although this antigen-coated latex agglutinated with an antierythropoietin antibody on a microplate, it did not undergo agglutination when the several antibodies of human albumin, human IgG, human transferrin, human haptoglobin and human $\beta_2$ microglobulin were added. Furthermore, agglutination did not take place when the antigen-coated latex was added after the antierythropoietin antibody was neutralized by the addition of erythropoietin. Again, although the antierythropoietin antibody was added under identical conditions to a latex that had not been coated with erythropoietin, agglutination did not take place. It was thus confirmed that this antigen-coated latex reacts specifically with the antierythropoietin antibody and agglutinates.

The diluent used was one obtained by adding BSA to a 1/60 M phosphate-buffered physiological saline (pH 7.2) to a concentration of 0.1%.

EXAMPLE 2

Lyophilization of the antigen-coated latex

The antigen-coated latex prepared in Example 1 was suspended in a diluent containing 0.5% by weight of glycine and 0.7% by weight of dextran [Dextran (molecular weight 200,000-300,000) produced by Wako Jyunyaku Co.] to a concentration of 2.5%. After quick-freezing it in liquid nitrogen, it was lyophilized.

EXAMPLE 3

Determination of erythropoietin

A diluent in an amount of 0.025 ml was poured into each well of a V-type microplate. To the first well 0.025 ml of serum was added. On the other hand, 75 miu/ml of a standard erythropoietin was added to the first well of another line, and progressively diluted with a diluter by the serial twofold dilution method. All of the wells were then admixed with 0.025 ml of an antierythropoietin antibody diluted in advance with standard erythropoietin so that the sixth well would be the end point. The mixtures were then held at room temperature for 30 minutes, after which 0.05 ml of the antigen-coated latex obtained in Example 1 was added to each well. The mixtures were then thoroughly mixed in a micromixer and left to stand at room temperature for at least 10 hours. The end point of inhibition of agglutination was then measured, and the erythropoietin concentration was calculated by comparison with the standard erythropoietin.

The results obtained when the concentration of erythropoietin in human serum was determined by this method are shown in the following table.

| Determination of Serum Erythropoietin (Agglutination Inhibition Value) | | | | | | | | | | | | | |
| --- | --- | --- | --- | --- | --- | --- | --- | --- | --- | --- | --- | --- | --- |
| No. | 1 | 2 | 3 | 4 | 5 | 6 | 7 | 8 | 9 | 10 | 11 | 12 | miu/ml |
| Standard solution 75 miu/ml | − | − | − | − | − | − | + | + | + | + | + | + | |
| Healthy adult (27-year-old-male) | − | − | − | − | − | + | + | + | + | + | + | + | 37.5 |
| Healthy adult (46-year-old male) | − | − | − | − | − | − | + | + | + | + | + | + | 75 |

-continued

Determination of Serum Erythropoietin (Agglutination Inhibition Value)

| No. | 1 | 2 | 3 | 4 | 5 | 6 | 7 | 8 | 9 | 10 | 11 | 12 | miu/ml |
|---|---|---|---|---|---|---|---|---|---|---|---|---|---|
| Aplastic anemia (18-year-old female) | − | − | − | − | − | − | − | − | − | − | − | + | 2400 |
| Aplastic anemia (24-year-old male) | − | − | − | − | − | − | − | − | − | − | + | + | 1200 |
| Hypoferric anemia (51-year-old female) | − | − | − | − | − | − | − | − | + | + | + | + | 300 |
| Chronic renal insufficiency (47-year-old male) | − | + | + | + | + | + | + | + | + | + | + | + | 2.3 |
| Chronic renal insufficiency (39-year-old male) | − | − | − | + | + | + | + | + | + | + | + | + | 9.3 |

−: Unagglutinated
+: Agglutinated

EXAMPLE 4

A diluent was added to the antigen-coated latex obtained in Example 2 such that the concentration of the latex particles would be 0.25%, after which the operation was carried out as in Example 3 to determine the erythropoietin contained in the serum. The results obtained were the same as those of Example 3.

As apparent from the foregoing results, the erythropoietin in blood was a high value in the case of hypoferric anemia and an abnormally high value in the case of aplastic anemia but was an abnormally low value in the case of renal anemia. It can thus be said that the determination of erythropoietin of anemic patients is extremely useful in diagnosing the cause of anemia in these patients, as well as for determining the extent of the disease.

The use of the antigen-coated latex of this invention makes it possible to very easily determine the level of erythropoietin with an extremely small quantity of the sample and moreover without the need for any pretreatment of the sample. The method of the present invention can thus be said to be especially suitable for use in clinical diagnosis.

We claim:

1. A composition for determining human erythropoietin, said composition consisting essentially of synthetic polymeric latex particles and hyman erythropoietin coated on the surfaces of said latex particles.

2. The composition of claim 1 wherein the latex particles have an average particle diameter of from 0.01 to 10 microns.

3. The composition of claim 1 wherein the latex particles have a specific gravity of from 0.9 to 1.4.

4. The composition of claim 1 including a stabilizer selected from the group consisting of the amino acids and dextran.

5. The composition of claim 1 wherein the synthetic polymeric latex particles are particles of a styrene-type synthetic polymeric latex selected from the group consisting of the latexes of styrene polymer, styrene copolymers and the carboxylated or amino-containing carboxylated products thereof.

6. The composition as defined in claim 1 comprising styrene-type synthetic polymeric latex particles having an average particle diameter of from 0.01 to 10 microns and a specific gravity of from 0.9 to 1.4 and being particles of a latex selected from the group consisting of the latices of styrene polymer, styrene copolymers, and the carboxylated or amino-containing carboxylated products thereof; human erythropoietin coated on the surfaces of said latex particles; and a stabilizer composed of glycine in a concentration of 0.2 to 2% by weight and dextran in a concentration of 0.3 to 3% by weight.

7. A method for determining human erythropoietin in human urine or serum by the microtiter method comprising adding prescribed amounts of antibody to progressively diluted samples of said human urine or serum to neutralize erythropoietin in the samples; adding to the samples a composition consisting essentially of synthetic polymeric latex particles having a specific gravity of about 1.1 to 1.3 and having human erythropoietin coated on the surface of said latex particles; and observing the agglutination reaction caused by said latex and any antibody remaining unneutralized.

8. The method of claim 7 wherein said synthetic polymeric latex particles have an average diameter of from 0.01 to 10 microns and are selected from the group consisting of the latexes of styrene polymer, styrene copolymers, and the carboxylated or amino-containing carboxylated products thereof; said composition containing additionally a stabilizer composed of glycine in a concentration of 0.2 to 2% by weight and dextran in a concentration of 0.3 to 3% by weight.

* * * * *

UNITED STATES PATENT AND TRADEMARK OFFICE
CERTIFICATE OF CORRECTION

PATENT NO. : 4,321,058
DATED : March 23, 1982
INVENTOR(S) : TETSUO TOMIYAMA, ET AL.

It is certified that error appears in the above—identified patent and that said Letters Patent is hereby corrected as shown below:

On the title page,

Correct Assignee to read:

-- Seikagaku Kogyo Co., Ltd. --.

Claim 1, Column 9, line 40, change "hyman" to --- human ---

Signed and Sealed this

Seventeenth Day of April 1984

[SEAL]

Attest:

Attesting Officer

GERALD J. MOSSINGHOFF

Commissioner of Patents and Trademarks